United States Patent
Jorneus et al.

Patent Number: 5,873,720
Date of Patent: Feb. 23, 1999

[54] SPACING MEMBER

[75] Inventors: Lars Jorneus, Frillesas; Lennart Loof, Vastra Frolunda, both of Sweden

[73] Assignee: Nobel Biocare AB, Gothenburg, Sweden

[21] Appl. No.: 545,614
[22] PCT Filed: Mar. 2, 1995
[86] PCT No.: PCT/SE95/00217
§ 371 Date: Jan. 19, 1996
§ 102(e) Date: Jan. 19, 1996
[87] PCT Pub. No.: WO95/23561
PCT Pub. Date: Sep. 8, 1995

[30] Foreign Application Priority Data

Mar. 3, 1994 [SE] Sweden .................................. 9400727

[51] Int. Cl.⁶ ...................................................... A61C 8/00
[52] U.S. Cl. ........................................... 433/172; 433/173
[58] Field of Search ...................................... 433/172, 173, 433/174, 175

[56] References Cited

U.S. PATENT DOCUMENTS

| | | | |
|---|---|---|---|
| 4,780,080 | 10/1988 | Haris ........................................ | 433/174 |
| 5,286,195 | 2/1994 | Clostermann ............................ | 433/172 |
| 5,302,126 | 4/1994 | Wimmer et al. ......................... | 433/174 |
| 5,368,160 | 11/1994 | Leuschen et al. ....................... | 433/174 |
| 5,431,567 | 7/1995 | Daftary .................................... | 433/173 |
| 5,527,182 | 6/1996 | Willoughby ............................. | 433/172 |
| 5,622,500 | 4/1997 | Niznick ................................... | 433/173 |

FOREIGN PATENT DOCUMENTS

| | | |
|---|---|---|
| 0 291 103 | 11/1988 | European Pat. Off. . |
| 0 323 421 | 7/1989 | European Pat. Off. . |
| 0 419 431 | 3/1991 | European Pat. Off. . |

OTHER PUBLICATIONS

Nobelpharma Product Catalog 1991, Components for the Standard Restorative Procedure, p. 12.

*Primary Examiner*—Cary E. O'Connor
*Attorney, Agent, or Firm*—Pollock, Vande Sande & Amernick

[57] ABSTRACT

A spacing member for a securing element (fixture) permanently anchored in the jawbone. The spacing member comprises a substantially sleeve-shaped spacing element to be fitted on the securing element and a separate spacing screw. The spacing screw has an elongate, unthreaded middle portion and a threaded portion at its tip for engaging with an internally threaded bore in an upper part of the securing element. The sleeve-shaped spacing element includes a passage extending longitudinally therethrough for receiving the spacing screw. The passage has an internally threaded portion for engaging with the spacing screw, so that the spacing screw, after it has been threaded through the threaded portion, is joined together with the spacing element, and a recess in an upper part of the passage. The recess has a non-circular geometry for facilitating application of a counter-holding instrument in order to prevent the tightening force from being transmitted down into the securing element when the sleeve-shaped spacing element is fitted on the securing element.

8 Claims, 1 Drawing Sheet

SPACING MEMBER

FIELD OF THE INVENTION

The present invention relates to a spacing member for a securing element (fixture) permanently anchored in the jawbone, comprising an essentially sleeve-shaped spacing element intended to be fitted on the securing element by means of a separate spacing screw. The screw is provided with an elongate, unthreaded middle area and, at its tip, an externally threaded portion which is intended to engage with an internally threaded bore in the upper part of the securing element. The sleeve-shaped spacing element is provided with a passage having an internally threaded portion for the spacing screw, so that the spacing screw, after it has been threaded through this portion, is integrally connected to the spacing element.

BACKGROUND OF THE INVENTION it is already known to anchor a tooth prosthesis permanently in the jaw with the aid of securing elements in the form of titanium screws, so-called fixtures, which are implanted in the jawbone. The screws are anchored in holes in the bone so that the upper part of the screw is situated to level with or just below the upper surface of the jawbone. The screw is then covered over with a flap of mucous membrane and is left unloaded for a rest period of 3–6 months in order for the bone to fix firmly to the implanted screw and form a unit therewith. After the rest period, the screw is exposed, and a spacing member, also preferably of titanium, is screwed into place, after which the tooth prosthesis is anchored on the spacing member. The tooth prosthesis must in this case be exactly matched to the appearance of the jaw with the titanium fixtures implanted.

In order to meet the individual requirements of different patients, there are a number of different types of spacing members on the market. The BRÅNEMARK SYSTEM, which is marketed by Nobelpharma AB, includes a number of standard spacers which consist of spacing cylinders of different lengths, from 3 to 10 mm, and separate spacing screws for securing the spacer on the fixture. The base portion of the spacing cylinders is adapted to the hexagon shape of the fixture, so that positive locking is achieved when this portion is applied to the fixture.

In order to improve the aesthetic result of a tooth reconstruction, other types of spacing members are also already known, see for example EP 0 291 103, EP 0 323 421 and ER 0 419 431. These spacing members also comprise an essentially cylinder-shaped spacer and a separate spacing screw.

In some cases it may be difficult to decide on the final type of spacing member which is to be used, or it may also be difficult to determine exactly the correct length of the spacer. In these cases, so-called healing spacers are used which are connected to the fixture temporarily while the final artificial crown is being made and tried out on the patient, but which are then replaced by the permanent spacer. Using a particular healing spacer improves the conditions for favorable incorporation of the mucous membrane, since the mucous membrane can be given a contour which is adapted to the contour of the permanent spacer. The healing spacers are similar to the standard spacers, but the sleeve and the screw are made in one piece. For thin reason, the healing spacers do not provide for positive locking to the upper part of the fixture.

Spacers which are made in this way, i.e. in which the screw and the actual spacing sleeve are in one piece, suffer from a number of disadvantages:

It is not possible to apply counterholding when the spacer is connected to the fixture, i.e. the entire tightening force is transmitted down to the fixture (the implant) which thereby runs a potential risk of becoming loose when the spacer is being tightened or loosened.

On account of the large diameter of the screw head, a considerable torque is required in order to achieve proper tightening of the screw connection.

Should the spacer become loose, the screw may be subjected to a rocking movement, which can lead to the spacer breaking.

All spacers have had a circular symmetrical-shape. since the spacer cannot be positioned.

It is not possible to use one material for the screw and another material for the actual spacer, although this may be desirable since the spacer must be made of a biocompatible material and the screw should be made of a material with high strength.

All these disadvantages can be overcome by using a spacing member which has a separate spacing screw, but this is at the expense of the components being more difficult to handle. Since the components are small, and since the space for handling them is also small, this represents a serious disadvantage in the case of those spacing members which are not made as one piece only. There is also a potential risk of dropping the small spacing screw and of the latter slipping down the patient's throat.

It is already known to arrange a spacing member with a separate screw in such a way that the screw and the spacer are made integral by means of the screw having been screwed through a threaded passage in the spacing sleeve, see EP 0 456 777. In this way it is possible to facilitate use of the spacing member and to reduce the risk of components being dropped. However, despite the fact that the spacing member has a separate spacing screw, it has the same disadvantages as regarding the risk of the tightening force being transmitted down to the fixture when the spacing member is fitted. The frictional force between the spacing sleeve 2 and the fixture 1 is in fact quite sufficient to be able to transmit the tightening force to the fixture.

Moreover, in the construction which is shown in EP 0 456 777, the spacing sleeve 2 is provided with an internal thread 23 at the far bottom of the continuous passage. This means that the threaded portion 34 of the spacing screw, after it has been screwed via the thread 23, comes to be situated completely outside the spacing sleeve 2. This makes it difficult to fit the spacing member to the fixture 1, since both the spacing sleeve and the screw have to be fitted simultaneously to the fixture. There is admittedly a free area (unthreaded part) 14 in the fixture which accommodates the threaded portion 34 of the spacing screw before the screw is screwed firmly into the threaded bore 13 of the fixture, but the majority of today's existing fixtures have a bore which is threaded right to the top, which makes it problematic to fit a spacing member, of the type which is shown in the European patent, in terms of getting the spacing screw into the correct position for threading-in, and at the same time the spacing sleeve cannot assume its final position in relation to the fixture. This position can be assumed only after the spacing screw has been screwed down a certain distance in the fixture.

A further disadvantage of the known construction is that the spacing screw, after it has been screwed via the thread 23 in the spacing sleeve, has its entire threaded portion 34 exposed, which increases the risk of damage to the thread upon handling, for example during transport.

SUMMARY OF THE INVENTION

An object of the present invention is to provide a spacing member which is easy to handle and which simplifies fitting on today's existing fixtures, and at the same time to minimize the risk of the tightening force being transmitted down to the fixture.

A further object of the invention is to provide an improved temporary spacing member, so-called healing spacer, which affords increased possibilities of controlling soft-tissue ingrowth and which also facilitates the choice of the permanent spacing member.

According to the invention, is the spacing member the part of the spacing sleeve directed away from the fixture has a non-circular geometry for a counterholding instrument, preferably in the form of an upper recess in the screw passage of the spacing sleeve. Providing the spacing sleeve with such a counterholding piece reduces the risk of transmitting the tightening force down into the fixture when the spacing screw is being tightened.

According to an advantageous embodiment of the spacing member, the passage for the spacing screw further comprises, in that part of the spacing sleeve which is directed towards the fixture, an unthreaded portion (clearance) within which the threaded portion of the spacing screw can be completely or partially accommodated before the fitting of the spacing member. In this way the spacing member can be better handled, as regards both storage/ transport and the fitting of the spacing member on the fixture.

In the case where the spacing member is intended to be used temporarily, during a healing period, the spacing sleeve is preferably provided with outer depth markings in order to facilitate the choice of the final spacer (length).

BRIEF DESCRIPTION OF THE DRAWINGS

An example of how the spacing member may appear is shown on the attached drawing, in which.

DETAILED DESCRIPTION OF THE PREFERRED EMBODIMENT(S)

Figure 1:
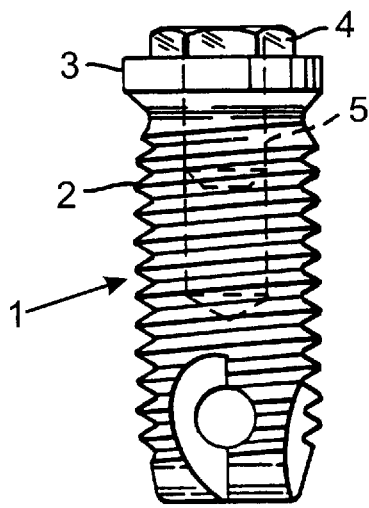
FIG. 1 shows a known securing element (fixture) to which the spacing member is to be connected.
Figure 2:
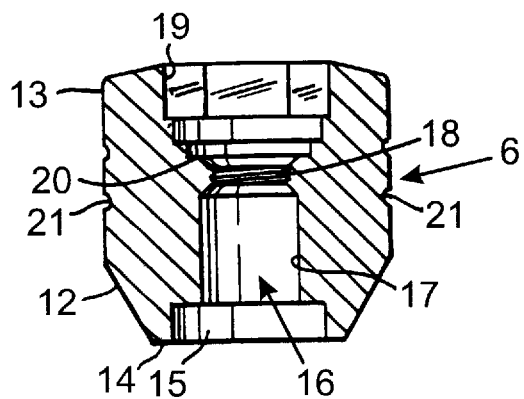
FIG. 2 shows the spacing element.
Figure 3:
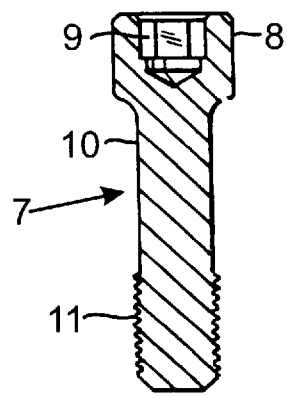
FIG. 3 illustrates the spacing screw.

The figures show a spacing member, according to the invention, which is intended to be connected to a securing element in the form of a cylindrical titanium screw (fixture) 1. The screw 1 which has an external thread 2 and is intended to be introduced into a pre-drilled hole in the jawbone for permanent anchoring of a tooth prosthesis. The external thread terminates at the top in a wider cylindrical flange 3 having a flat shoulder against which the spacing member bears after attachment. The fixture has an upper hexagonal portion 4 intended to cooperate with a tool used for installation of the fixture, and an upper central bore 5 with an internal thread in which the spacing screw engages upon fitting of the spacing member.

The spacing member comprises an essentially sleeve-shaped spacing element 6 and a spacing screw 7 provided with a screw head 8 with a recess 9 for application of a tool, an elongate middle area 10, and a threaded portion 11 intended to engage with the internal thread in the upper bore 5 of the fixture for locking the spacing element 6 firmly to the fixture. The spacing element 6 has a lower, essentially conically narrowing portion 12 for passage through soft tissue, and with a smaller diameter which is adapted to the outer diameter of the flange 3 of the fixture, and an upper essentially cylindrical portion 13 untended to extend up through the soft tissue. The conical portion 12 of the spacing element is provided at the bottom with a lower annular surface 14 for bearing against the flange 3 of the fixture, and an internal recess 15 whose diameter exceeds the greatest diameter of the hexagonal engagement portion 4 of the fixture. Thus, in contrast to conventional two-part spacing members, the spacing element is not positively locked to the fixture, which fact also facilitates fitting. The spacing sleeve takes up its position more easily than before, when there was a potential risk of the spacing sleeve being positioned obliquely and of the annular surface 14 thus not bearing fully against the flange of the fixture, in which case an X-ray examination was sometimes required in order to confirm this.

The lower recess 15 of the spacing element connects to a central passage 16 which extends through the spacing element in order to receive the spacing screw 7. The passage comprises a lower cylindrical recess 17 whose diameter exceeds the external thread diameter of the spacing screw so that a clearance is formed when the screw has been screwed through a threaded portion 18 of the passage. The length of the recess 17 preferably exceeds the length of the threaded portion of the spacing screw 7, so that this portion is accommodated in the recess. However, this does not apply to the shorter variants of spacing elements in which the threaded portion of the spacing screw is only partially accommodated in the recess 17. In the latter case, the length of the recess 17 exceeds the length of the threaded portion 18 of the passage The threaded portion can include a small number of thread turns, since the thread has only the function of joining together the two parts so that fitting is facilitated.

The passage 16 ends at the top in a wider recess 19 which forms a counterholder for an engagement tool, and an upper flat, annular shoulder 20 against which the screw head a of the spacing screw bears after fitting. The recess 19 can include any non-circular geometry whatsoever, for Rumple a hexagonal engagement as indicated in the figure. When the spacing member is being fitted, the recess 19 cooperates with a suitable counter-holding instrument in order to prevent transmission of the tightening force down into the fixture.

By providing the spacing element with an internal thread so that the two parts, spacing element and spacing screw, are joined together before fitting, and also by providing the spacing element with an internal recess, clearance, for the threaded portion of the spacing screw in that part which is directed towards the fixture, the fitting of the spacing element is further facilitated. During fitting, the spacing element in first placed so that its lower end surface 14 bears against the flange of the fixture. Only when the spacing element ham assumed its correct position, and is supported against the flange, does the dental surgeon need to ensure that the spacing screw is in correct engagement with the internal thread in the bore 5 of the fixture.

In the example which is shown in FIG. 1, the upper part 13 of the spacing element has a circular symmetrical part. However, this part can also have an asymmetrical configuration and can be set in the desired position because the spacing member is made up of two separate parts and the spacing element is not positively locked to the fixture. Such an asymmetrical configuration of the spacer can be particularly advantageous for so-called healing spacers which are used temporarily during the period in which the final, permanent spacer is being tried out and the prosthesis is being constructed, since the incorporation of the mucous membrane can then be controlled so that the latter acquires a desired contour during incorporation.

In the case where the spacing member is used an a healing spacer, i.e. temporarily, the outer surface of the upper part 13 of the spacing element can advantageously have (depth) markings 21 witch correspond to certain standard lengths of the final permanent spacers. In this way the selection of final spacer is facilitated since the markings give a good indication of the relation of a given spacer length to the depth of the soft tissue.

We claim:

1. A spacing member for a securing element (fixture) permanently anchored in the jawbone, the securing element having a flange with an upper engagement portion, said portion having a diameter, said spacing member comprising:

a substantially sleeve-shaped spacing element to be fitted on the securing element and a separate spacing screw;

said spacing screw having an elongate, unthreaded middle portion and a threaded portion at its tip portion for engaging with an internally threaded bore in an upper part of the securing element;

said sleeve-shaped spacing element having a lower end surface that bears against said flange of said securing element when the spacing element is connected to the securing element;

said sleeve-shaped spacing element also including a passage extending longitudinally therethrough for receiving said spacing screw, said passage having an internally threaded portion for engaging with the spacing screw, so that the spacing screw, after being threaded through said threaded portion, is joined together with the spacing element, and a first recess in an upper part of said passage, said recess having a non-circular geometry for facilitating application of a counter-holding instrument in order to prevent the tightening force from being transmitted down into the securing element when the sleeve-shaped spacing element is fitted on the securing element, said passage further including a lower unthreaded portion for accommodating at least partially said spacing screw joined through said threaded portion of said passage; said lower unthreaded portion terminating with a second recess having a diameter which exceeds the greatest diameter of an upper engagement portion of the fixture to permit the desired positioning of the spacing element on the securing element and bearing fully against the flange of the securing element (fixture).

2. A spacing member according to claim 1, wherein the passage of said sleeve-shaped spacing element further includes in a part which connects to the securing member, an unthreaded portion within which the spacing screw is to be at least partially accommodated before the fitting of the spacing member on the securing member.

3. A spacing member according to claim 1, wherein the length of the unthreaded portion of the passage considerably exceeds the length of the threaded portion of the passage.

4. A spacing member according to claim 2, wherein the unthreaded portion of the passage slightly exceeds the length of the threaded portion of the spacing screw.

5. A spacing member according to claim 3, wherein the outer surface of the upper part of the spacing element has a circular symmetrical form.

6. A spacing member according to claim 3, wherein the outer surface of the upper part of the spacing element has an asymmetrical form.

7. A spacing member according to claim 1, wherein the spacing member is a healing spacing member and the outer surface of the upper part of the spacing element is provided with depth markings corresponding to the lengths of the spacing elements in an existing spacer system, to facilitate selection of a permanent spacer to replace the healing spacing member used during a healing period.

8. A spacing member for a connection to a fixture permanently anchored in the jawbone, the securing element having a flange with an upper engagement portion, said portion having a diameter, said spacing member comprising:

a substantially sleeve-shaped spacing element to be fitted on the fixture and a separate spacing screw;

said spacing screw having an elongate, unthreaded middle portion and a threaded portion at its tip for engaging with an internally threaded bore in an upper part said sleeve-shaped spacing element having a lower end surface that bears against said flange when the spacing element is connected to the securing element; of the fixture;

said sleeve-shaped spacing element also including a passage extending longitudinally therethrough for receiving said spacing screw, said passage having 1) an internally threaded portion for engaging with the spacing screw, so that the spacing screw, after it has been threaded through said threaded portion, is joined together with the spacing element, 2) a lower unthreaded portion for accommodating at least partially said spacing screw joined through said threaded portion of said passage, 3) a first recess in an upper part of said passage, said recess having a non-circular geometry for facilitating application of a counter-holding instrument in order to prevent the tightening force from being transmitted down into the securing element when the sleeve-shaped spacing element is fitted on the securing element, and 4) inward shoulder for supporting a screw head after fitting and wherein the passage of the spacing element, in the part of the unthreaded portion which connects to the fixture, terminates with a second recess having a diameter which exceeds the diameter of an upper engagement portion of the fixture to permit the desired alignment (positioning) of the spacing element on the fixture.

* * * * *